United States Patent

Goble et al.

[11] Patent Number: 5,099,840
[45] Date of Patent: Mar. 31, 1992

[54] DIATHERMY UNIT

[76] Inventors: Nigel M. Goble, Chapel Cottage, Milton Combe, Yelverton, Devon, PL20 6HP, England; Colin C. O. Goble, 4 Bakers Court, Clive Road, Canton, Cardiff, CF5 4HJ, Wales, Wales

[21] Appl. No.: 299,949

[22] Filed: Jan. 23, 1989

[30] Foreign Application Priority Data

Jan. 20, 1988 [GB] United Kingdom ............... 8801177
Apr. 8, 1988 [GB] United Kingdom ............... 8808320

[51] Int. Cl.$^5$ ............................................. A61B 17/36
[52] U.S. Cl. .................................... 128/422; 128/804; 600/10
[58] Field of Search ............... 128/399, 419 N, 422, 128/402, 804, 421, 801; 600/9, 10, 13, 14

[56] References Cited

U.S. PATENT DOCUMENTS

| | | | |
|---|---|---|---|
| 3,964,487 | 6/1976 | Judson | 128/422 |
| 3,980,085 | 9/1976 | Ikuno | 128/422 |
| 4,069,827 | 1/1978 | Dominy | 128/422 |
| 4,092,986 | 6/1978 | Schneiderman | 428/422 |
| 4,124,030 | 11/1978 | Roberts | 128/422 |
| 4,126,137 | 11/1978 | Archibald | 128/422 |
| 4,189,685 | 2/1980 | Doss | 128/422 |
| 4,210,152 | 7/1980 | Berry | 128/422 |
| 4,372,319 | 2/1983 | Ichinomiya et al. | 128/422 |
| 4,429,698 | 2/1984 | Bentall | 128/422 |
| 4,527,550 | 7/1985 | Ruggera et al. | 128/422 |
| 4,679,561 | 7/1987 | Doss | 128/422 |

FOREIGN PATENT DOCUMENTS

| | | | |
|---|---|---|---|
| 0183534 | 6/1986 | European Pat. Off. | 128/422 |
| 570172 | 12/1975 | Switzerland . | |
| 1419660 | 12/1975 | United Kingdom . | |
| 8001461 | 7/1980 | World Int. Prop. O. | 128/422 |

OTHER PUBLICATIONS

Combined Electrosurgical Endoscopic Illumination and Headlamp Supply Unit—Service Manual.
Matburn Electrasect 3—Service Manual.
Matburn DLP 14—Instruction and Servicing Manual.

Primary Examiner—Edward M. Coven
Assistant Examiner—Jessica J. Harrison
Attorney, Agent, or Firm—Hale and Door

[57] ABSTRACT

A diathermy unit has a power oscillator with a resonant circuit arranged to be coupled to the load represented by the tissue to be treated. The resonant circuit includes a capacitor for connection in series with the load such that the resonant frequency varies with the load resistance. The resulting self-tuning of the oscillator allows improved matching of the oscillator to the load with consequent improved efficiency, a feature especially useful for a battery-powered unit. Regulation of the output power of the unit makes use of a feedback loop including an analogue multiplier for receiving signals representative of the power of the output stage, the resulting product signal being used to control pulse width modulation of the oscillator.

20 Claims, 3 Drawing Sheets

DIATHERMY UNIT

BACKGROUND OF THE INVENTION

This invention relates to a diathermy unit.

Conventional mains-powered diathermy units commonly apply radio frequency (r.f.) energy to the tissue to be treated at a power level determined by a power control circuit for controlling the amplitude of the r.f. signal generated by an r.f. oscillator. However, in practice, human tissue presents a widely variable electrical load, resulting in poor impedance matching of the r.f. output of the unit to the load in most circumstances so that, of the power generated, often only 20 per cent is dissipated in the load. Bipolar diathermy typically requires an applied r.f. power level of 10 watts, but in view of the inefficiency resulting from poor matching, a unit capable of generating much higher power levels than 10 watts is necessary, and for this reason a diathermy unit designed for hand held use would be large and unwieldy, especially if battery-powered.

SUMMARY OF THE INVENTION

In order to improve power efficiency, the present invention provides in accordance with one of its aspects, a diathermy unit operable to generate an output signal the frequency of which is variable and is dependent on a characteristic of the electrical load. Preferably the unit contains a self-tuning oscillator having a frequency-determining resonant circuit arranged to be coupled to the load represented by the tissue of the patient when the unit is in use and such that a variation in the resistance of the load causes a variation in the resonant frequency of the circuit. Such a resonant circuit may comprise parallel combination of a first capacitance and an inductance, which combination is coupled in series with a second capacitance across a pair of output terminals of the unit. With this arrangement, a decreased load resistance results in a decreased signal frequency and typically the values of the circuit are chosen to yield output frequencies differing by a factor of the square root of 2 between zero and infinite load resistances. Thus, with an infinite load resistance, the output frequency may be 500 kHz whereas at zero load impedance the frequency may be 353 kHz.

The inductor of the resonant circuit may constitute or form part of a step-up transformer or auto-transformer coupled between, for example, the supply and the output terminal of an amplifying device.

Preferably, self-oscillation is achieved by feeding a proportion of the energy produced in the resonant circuit back to the input of the amplifying device, which may be a metal oxide semiconductor field effect transistor (MOSFET). Devices of this type can be obtained with sufficient power handling capability for the required output power of the unit, and have a high input impedance coupled with a sufficiently fast switching speed respectively to minimize the effect of the feedback circuit on the Q of the resonant circuit and to allow operation at frequencies in the order of 500 kHz.

By allowing the frequency to vary with the load resistance, the energy loss in the output circuitry of the unit can be reduced over a wide range of load values compared with conventional diathermy units, with consequent benefits in efficiency and increased practicability of a hand-held battery-powered unit.

Control of the average power delivered to the load may be brought about by pulse width modulation of the oscillator. Known diathermy units have used pulse width modulation to adjust measured output power, but the actual power dissipated in the load varies depending on the load resistance for any given mark-to-space ratio.

According to a second aspect of this invention, a diathermy unit includes means for controlling the level of its output in response to a feedback signal, preferably a signal representative of the current drawn by the output stage. This allows the power to be adjusted in response to changes in load resistance. In particular, the feedback signal may be made representative of estimated power values by multiplication of a signal representative of the current drawn by the output stage and a signal representative of the supply voltage, allowing compensation for changes in the supply voltage which will occur if that voltage is unregulated, especially if the unit is battery-powered. In this connection, it will be understood that supply voltage regulation may be undesirable as it may involve significant power loss.

The applicants have found that one advantageous technique for obtaining a feedback signal representative of the actual output power of the unit is to monitor the voltage across a low resistance shunt in the supply to the output stage as a measure of the output stage current consumption and to apply this voltage, or one derived from it, to an input of an amplifier, the gain of which is variable in response to the level of a voltage, such as the supply voltage, governing the output power. The feedback signal obtained from the amplifier output is thus a function of the product of the current and, for example, the supply voltage.

An advantageous variable gain arrangement comprises an amplifier the gain of which is governed by the ratio of a feedback resistance and a series input resistance, one of these resistances being dynamically variable in response to the supply voltage level. Such variation may be achieved using a field effect transistor (FET) as one of the resistances, biased such that the source-to-drain resistance is substantially linearly related to the gate voltage. This near linear relationship may be achieved by biasing the FET so that the gate/-channel junction is forwardly biased over at least the majority of the operating range of the gate voltage, for instance by using a depletion mode FET in the enhancement region of its characteristic. In such circumstances the gate is no longer voltage controlled, but current controlled. It has been found that this biasing technique produces a response characteristic of sufficient linearity while minimizing offset inaccuracies when driving a differential gain-controlled amplifier.

Having thereby obtained a voltage representative of the output power, this voltage may be used to control pulse width modulation of the r.f. oscillator of the unit so as to complete a feedback loop for regulating power.

The invention is primarily applicable to a battery-powered bipolar diathermy unit but may also be used in mains-powered units, including unipolar units to improve their efficiency and power output characteristics. In a mains-powered unit, isolation of the output terminals of the unit may be provided by including a transformer with isolated windings in the resonant circuit.

BRIEF DESCRIPTION OF THE DRAWINGS

The invention will now be described by way of example with reference to the drawings in which.

DESCRIPTION OF PREFERRED EMBODIMENTS OF THE INVENTION

Figure 1:
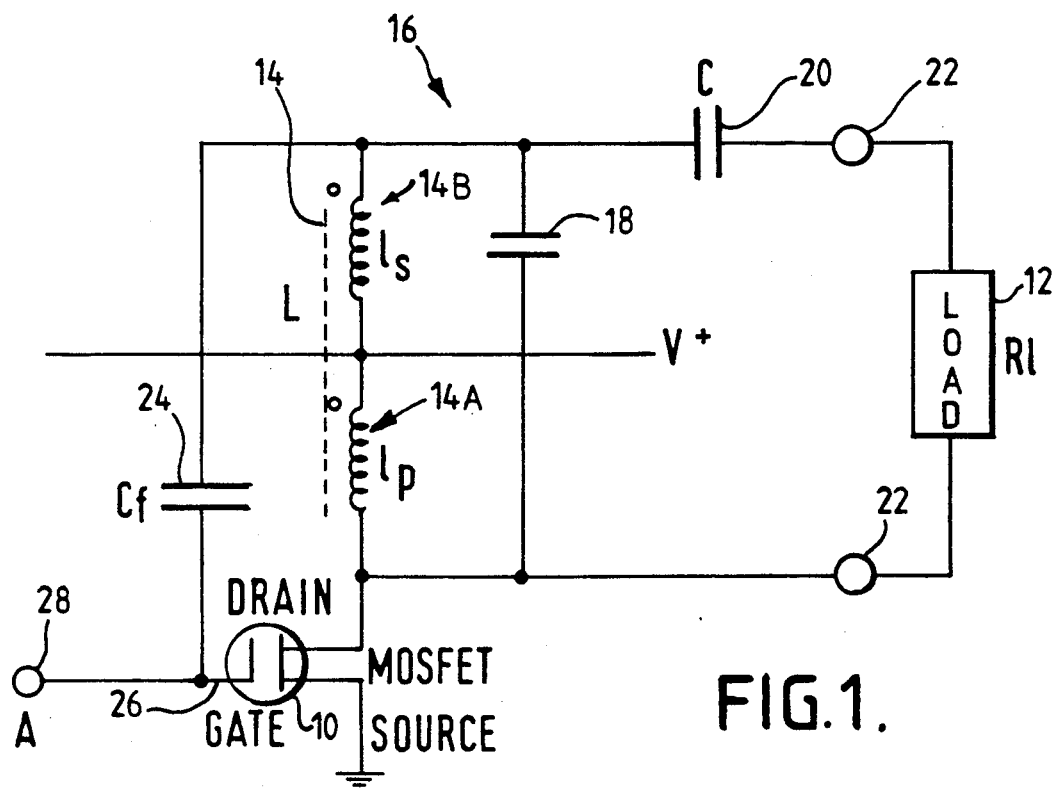
FIG. 1 is a simplified circuit diagram of an r.f. oscillator of a diathermy unit in accordance with the invention.

Referring to FIG. 1 of the drawings, a radio frequency oscillator suitable as a power oscillator for a diathermy unit has an amplifying device constituted by a power MOSFET 10 connectible to a load 12 in the form of human tissue via a step-up auto transformer 14 forming part of a resonant circuit 16. A d.c. supply line is coupled to the drain of the amplifying device via the primary winding 14A of the transformer 14, and the source is shown here connected to ground. The resonant circuit comprises the parallel combination of the series connected primary and secondary windings 14A and 14B of the transformer and a first capacitor 18, and a second capacitor 20 coupled in series with the parallel combination across a pair of output terminals 22 of the unit. Self-oscillation of the oscillator occurs due to positive feedback through a feedback capacitor 24 coupling one end of the parallel combination to the gate 26 of the device 10. In the preferred embodiment of the invention the gate 26 also acts as a control electrode for switching the oscillator on and off via terminal 28.

It will be appreciated that the resonant frequency of the resonant circuit 16 is dependent not only on the inductance value of the transformer 14 and its parallel capacitor 18, but also by the values of the second capacitor 20 and the load resistance. As a result, the oscillation frequency is governed by the load resistance which can vary widely depending on a number of factors related to the nature of the patient's tissue and the connection to it. Thus by making the oscillator the output stage of a diathermy unit, and allowing it to "self-tune" in response to the load, the unit may be matched to the load over a comparatively wide range of load resistances. Typically the capacitors have values within an order of magnitude of each other, i.e. the ratio of the values is less than 10 to 1, and in the present example are each 4.7 nanofarads.

By way of explanation, the Q (quality factor) of a resonant circuit is inversely proportional to the energy loss of that circuit. Energy losses within the inductance formed by the transformer 14 and the capacitor 18 are minimal in comparison to the dissipation in the load 12. When the resistance of the load approaches infinity, the applied voltage is proportional to $Q \times V_s$ ($V_s$ being the supply voltage) so that as the load resistance increases both the Q and the applied voltage become greater. Conversely, when the load resistance approaches zero, the current in the resonant circuit is relatively high and is proportional to $Q \times I_s$ where $I_s$ is the supply current. Reducing the load resistance in these circumstances minimizes the energy loss and consequently both the Q and the applied current are increased. This relationship holds provided the oscillator operates at the prevailing resonant frequency.

Use of a power MOSFET (such as type no. IRFZ 20) allows a power output of 10 watts to be achieved while requiring only a small feedback current due to the high impedance of the gate of the device.

The ratio of the inductances of the primary and the secondary is dependent on the power required, the supply voltage (V+) and the matched load resistance, which is the resistance at which Q approaches 1. The secondary voltage is dependent on Q, thus the feedback energy to the gate of the amplifying device 10 will also change with load resistance.

Figure 2:
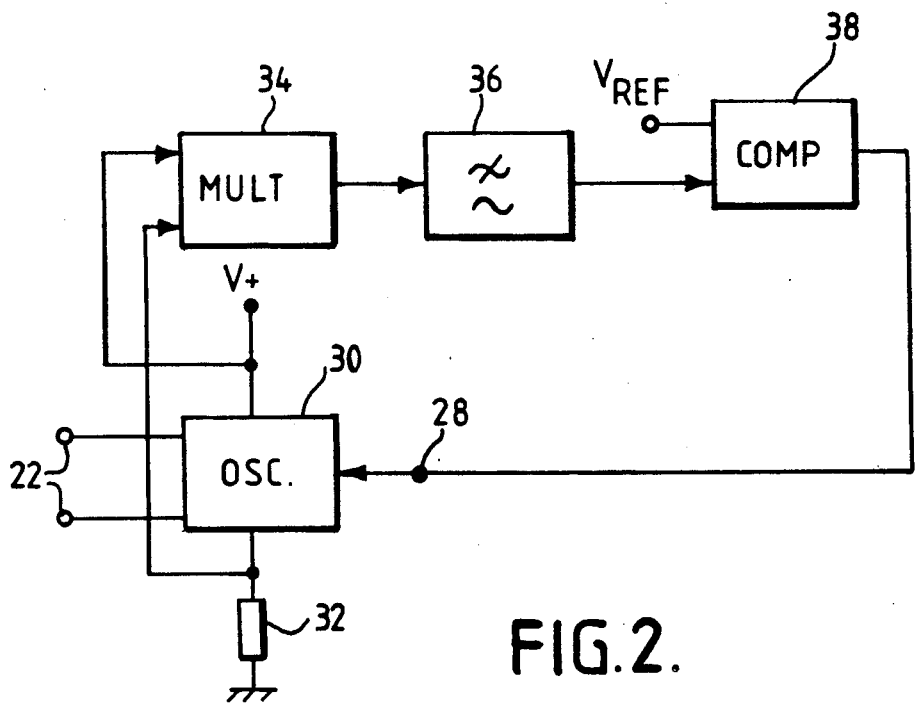
FIG. 2 is a block diagram of a diathermy unit in accordance with the invention.

The preferred embodiment of the invention is a diathermy unit which uses the above described power oscillator as the source of r.f. energy and as the output stage of the unit, as shown in FIG. 2, where the oscillator is indicated by the reference numeral 30. To control the overall power output of the unit, the oscillator 30 is pulse-width modulated via the oscillator control input 28, the mark-to space ratio of the pulses applied to the control input being governed by a feedback control loop as shown. The loop is characterised by the generation of a signal representing an estimate of the actual power applied to the load via the terminals 22. In this embodiment, the estimate is based upon the assumption that the power output is approximately proportional to the product of the d.c. current drain of the oscillator 30 and the supply voltage level. This technique has the advantage that the mark-to-space ratio of the oscillator output can be varied in response to changes in load impedance as well as supply voltage level, allowing a selected power level to be maintained and yielding an improvement in performance into differing loads.

The supply voltage level is easily monitored. The current drain is measured by monitoring the voltage drop across a shunt resistance 32 connected in the oscillator supply. The unit has an analogue multiplier 34 for generating the required signal representative of the product of these two quantities, the product being formed preferably by feeding the signal from the shunt to an input of an amplifier the gain of which is variable in proportion to the supply voltage level, as will be described below.

Having derived a signal representative of the output power, this signal is filtered by a low-pass filter 36 and then compared with a reference voltage $V_{REF}$ in a comparator 38. Feeding the "power error" switching signal obtained at the output of the comparator 38 to the control terminal 28 of the oscillator 30 has the effect of pulse modulating the oscillator, the frequency of modulation being dependent on time constants and switching threshold levels in the feedback loop. Power adjustment may be performed by varying the reference voltage $V_{REF}$, preferably in a series of steps. At the maximum power setting the arrangement of the circuitry is such that the mark-to-space ratio of the oscillator control signal is equal to or approaching 1 when the supply voltage is at a minimum operating level and the load impedance is at the extremes of the allowed range. At all other times the mark-to-space ratio is less.

The process of measuring the output power and controlling the oscillator will now be described in more detail with reference to the circuit diagram of FIG. 3 and the graph of FIG. 4.

Figure 3:
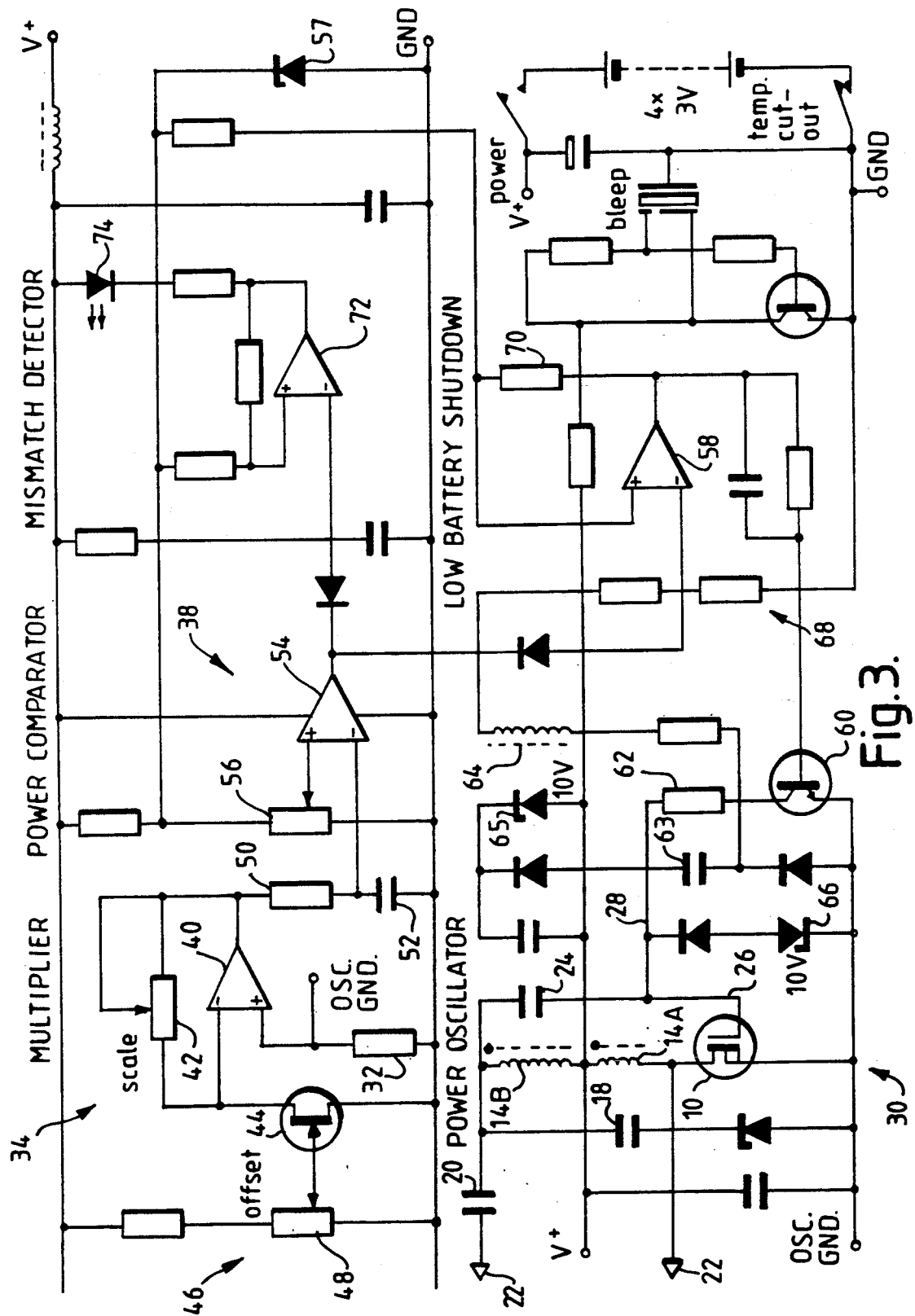
FIG. 3 is a circuit diagram of a preferred diathermy unit.

Referring to FIG. 3, the voltage from the current sensing shunt resistance 32, here a resistor of 20 milliohms, is fed to the non-inverting input of an operational amplifier 40, the gain of which is determined by the ratio of the feedback resistance 42 and the series input resistance of a field-effect transistor (FET) 44. In order for the gain of the amplifier 40 to be varied linearly with the supply voltage level, the gate of the FET 44 is coupled to a potential divider 46 connected across the voltage supply so as to bias the FET which is a depletion type into the enhancement region, i.e. with the gate forward biased. In this way a substantially linear channel resistance characteristic is combined with the current driven characteristic of a bipolar transistor, which minimizes inaccuracies due to the offset at the input of the operational amplifier 40.

Figure 4:
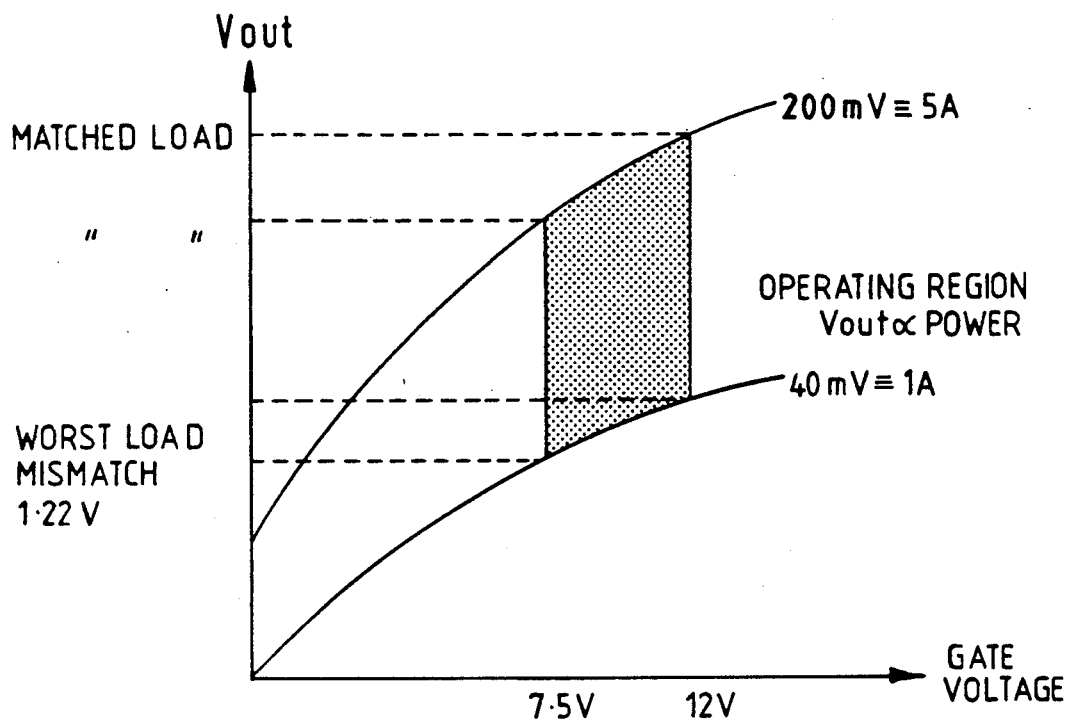
FIG. 4 is a graph illustrating the characteristics of an analogue multiplier arrangement.

The graph of FIG. 4 illustrates the variation of the voltage obtained from the output of amplifier 40 with varying gate voltage at two different oscillator current levels. The shaded region indicates the operating region of the graph if the gate voltage is coupled directly to the voltage supply and the supply is considered to vary between 7.5 v and 12 v, as it might if battery supplied. In this region the characteristic is approximately linear for any given current within the range shown, but the tangents of the curves do not intersect the supply voltage axis at zero, leading to an offset power error.

Figure 5:
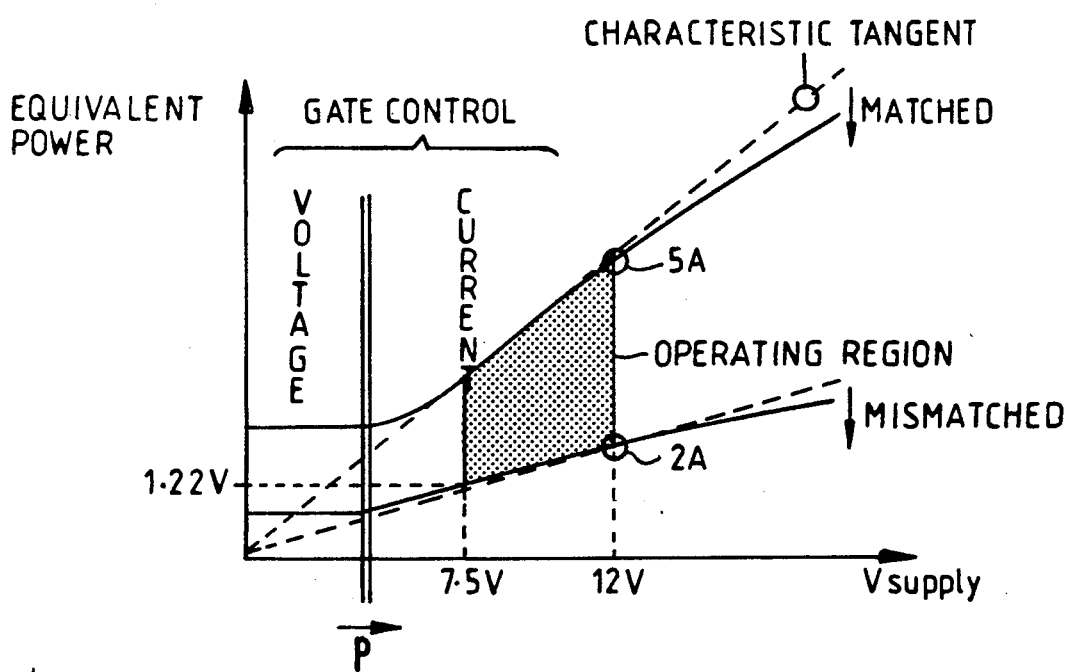
FIG. 5 is a graph similar to that of FIG. 4 illustrating the characteristics of a modified analogue multiplier arrangement.

By connecting the gate instead to the tap of a potential divider, as shown in FIG. 3, the origin of the graph can effectively be moved to the left as shown in FIG. 5, although the biasing is still such that over the permitted range of the supply, the device is operated in the enhancement mode. It will be seen that the output voltage of the amplifier 40 is now proportional to both oscillator current and supply voltage. In the circuit of FIG. 3, a variable resistor 48 in the potential divider 46 allows the offset to be set if required. The feedback resistance is also presettable to allow adjustment of the gain/supply voltage ratio.

In practice, the characteristic of FIG. 5 does exhibit a slight curve which can be used to advantage in tailoring the multiplier response to the actual, as opposed to estimated or predicted, output power of the unit thereby largely compensating for any inaccuracy arising from the assumption that the power dissipated in the load is proportional to the product of the supply voltage and the oscillator current (due to variations in efficiency of the oscillator over the supply voltage range).

The FET 44 is selected for low gate current, i.e. high transconductance, and type no. BF 256 C has been found suitable.

Referring again to FIG. 3, the signal from the multiplier 34 is low-pass filtered by the resistor 50 and the capacitor 52 and fed to another operational amplifier 54, this amplifier being connected as a comparator, having one input coupled to an adjustable voltage reference generated by variable resistance 56 connected across a 1.225 v zener diode 57.

The output of the comparator can be seen to be equivalent to the oscillator requirement in that its output is high when the oscillator is required to be "on" to increase power.

Yet a further operational amplifier 58, connected as another comparator, in normal operation inverts the "power error" signal from the first comparator 54 and drives a switching transistor 60 coupled via resistor 62 and capacitor 63 to the gate of the MOSFET 10.

The rate of change of the "power error" signal is determined by the slew rate of the amplifier 54 (typically 0.5 v per microsecond) and the time constant for the low pass filter formed by capacitor 52 and resistor 50 (typically 10 nanofarads and 180 kilohm respectively). A combination of the rate of change of the power error signal and the threshold voltages, dictated by the hysteresis loop of amplifier 58, determine the modulation frequency.

Switching the oscillator off is merely accomplished by stealing the MOSFET gate drive by making switching transistor 60 conductive. Starting the oscillator again, however, requires a transient "kick", which is generated by the inductor 64 in the collector circuit of the transistor 60.

When the unit drives a high resistance load, the alternating voltage generated across the resonant circuit 14 can be sufficient that the feedback voltage applied via capacitor 24 to the gate of the MOSFET 10 can exceed the maximum permitted gate voltage of the device. This possibility is avoided by clamping the gate to a maximum voltage (+20 v) determined by a zener diode 65 coupled to the positive supply. To maintain an average gate voltage of one half of the supply voltage (for 50% mark-space switching) a second zener diode 66 clamps the gate to a minimum voltage of −5 v (The gate switching threshold is approximately 8 v). The clamping arrangement has the advantage that excess feedback energy is fed back to the supply, reducing energy loss.

The unit incorporates means for shutting down the oscillator when the supply voltage decreases beyond a set lower level, in this case 7.5 v. Comparator 58 uses as its reference voltage the output of the 1.22 5 V zener diode 58 which is applied to the non-inverting input. The other input, in the absence of a low "power error" signal from comparator 54, is at a voltage determined by the supply voltage and the potentiometer 68, and the latter is arranged to generate a d.c. level of 1.225 v when the supply voltage is 7.5 v. Thus, when the voltage decreases below 7.5 v, the oscillator is turned off via switching transistor 60. The resistor 70 provides the hysteresis referred to earlier. This has the effect of allowing the oscillator to be restarted when a battery supply recovers after a prolonged period of operation causing the supply voltage to fall below 7.5 v.

A circuit for warning of a power output below that selected is provided by another operational amplifier 72. A continuous high output from comparator 54 indicates that, as a result of reduced battery output, the oscillator is being required to run continuously. Under such circumstances the selected power output cannot be guaranteed. This condition causes a light emitting diode 74 to be energised by the amplifier 72, which acts as a monostable.

The output of amplifier 58 may remain high under two possible conditions; load mismatch and low battery power. This allows an indication of battery condition to be provided. Under particular mismatch loads the output will fail to reach the selected power level, particularly at the maximum power setting of the potentiometer 56. The maximum power available will, in these conditions, be particularly dependent on supply voltage. A convenient load mismatch is infinite impedance on an open circuit output. The power setting control may also be graduated with battery condition bands so that, with the unit activated under zero load, the control may be adjusted to find the point at which the battery condition light emitting diode 74 operates. Battery condition is then read from the scale.

What is claimed is:

1. A diathermy unit comprising oscillator means for generating an oscillatory radio frequency output signal, the oscillator means having at least one terminal for direct electrical connection to an electrical load in the form of living tissue and means for causing the radio frequency of said oscillatory output signal to vary automatically in response to the resistance of the living tissue load while the unit is in use.

2. A diathermy unit according to claim 1, including a self-tuning oscillator including means which, when the unit is coupled to the load, form, in conjunction with the load, an oscillator-frequency-determining resonant circuit whose resonant frequency varies according to electrical resistance of the load.

3. A diathermy unit according to claim 2, wherein the resonant circuit comprises a parallel combination of a first capacitance and an inductance, which combination is coupled to a second capacitance such that the combination and the second capacitance are coupled together in series between a pair of output terminals of the unit.

4. A diathermy unit according to claim 3, wherein the inductance constitutes a transformer or forms part of a transformer.

5. A diathermy unit according to claim 2, wherein the oscillator is a power oscillator forming the output stage of the unit.

6. A diathermy unit according to claim 5, wherein the oscillator includes a power MOSFET coupled to the resonant circuit.

7. A diathermy unit according to claim 5, including diode clamping means for limiting feedback to the oscillator device.

8. A diathermy unit according to claim 7, wherein the clamping means comprises a zener diode coupled between an input connection of the oscillator device and a power supply for the oscillator.

9. A diathermy unit according to claim 1, including an oscillator device, a step-up transformer arranged such that the oscillator device develops an output across a primary winding of the transformer, and a pair of output terminals for coupling to a load in the form of living tissue, the step-up transformer forming part of a resonant circuit having a resonant frequency which is load dependent, and having a secondary winding coupled to the output terminals.

10. A diathermy unit according to claim 9, wherein the transformer is an auto-transformer.

11. A diathermy unit according to claim 9, wherein the resonant circuit further includes a first capacitance coupled in parallel with an inductance formed by the transformer and a second capacitance in series between the resulting parallel combination and one of the output terminals.

12. A diathermy unit according to claim 1, further comprising pulse modulation means for modulating the output signal by a pulsed modulation signal of variable mark-to-space ratio.

13. A diathermy unit according to claim 1, including an analogue multiplier arranged to receive signals representative of the voltage and current respectively of the said output signal, comparison means coupled to receive a product signal from the analogue multiplier for comparing the product signal with a reference signal, and means for varying the power of the said output signal in response to the product signal thereby to regulate the output power of the unit to a predetermined level.

14. A diathermy unit according to claim 13 wherein the analogue multiplier comprises an amplifier and a resistance associated with and governing the gain of the amplifier, wherein the resistance comprises a field-effect transistor arranged to have its gate forward biased, the multiplier having a first input coupled to the gate of the field-effect transistor and a second input formed by or coupled to an input of the amplifier.

15. A diathermy unit, according to claim 14, wherein the amplifier is a differential amplifier having an inverting input and a non-inverting input, a first resistance coupled between the inverting input and a ground or a.c. ground point, and a second resistance coupled between the inverting input and an output of the amplifier, wherein the field-effect transistor forms at least part of either the first or the second resistance, and wherein the non-inverting input forms or is coupled to the second input of the amplifier.

16. A diathermy unit according to claim 14, wherein the field-effect transistor is a depletion type field-effect transistor arranged to be biased into the enhancement region of its characteristic.

17. A diathermy unit according to claim 14 including a shunt resistance coupled to pass a current representative of said output signal current, the first input of the multiplier being connected to receive a voltage related to the voltage of said output signal and the second input of the amplifier being connected to one end of the shunt resistance.

18. A diathermy unit according to claim 1 which is battery-powered.

19. A diathermy unit according to claim 1 wherein said diathermy unit is a bipolar diathermy unit.

20. A diathermy unit according to claim 1 wherein said diathermy unit is a unipolar diathermy unit.

* * * * *